(12) United States Patent
Aikawa et al.

(10) Patent No.: US 9,066,977 B2
(45) Date of Patent: *Jun. 30, 2015

(54) METHOD OF UTILIZATION OF COMBINATION OF BENZOPHENONE DERIVATIVE OR SALT THEREOF AND IMMUNOSUPPRESSING AGENT, AND PHARMACEUTICAL COMPOSITION COMPRISING THESE COMPONENTS

(75) Inventors: Yukihiko Aikawa, Toyama (JP); Shunichi Shiozawa, Kobe (JP)

(73) Assignee: TOYAMA CHEMICAL CO., LTD., Tokyo (JP)

( * ) Notice: Subject to any disclaimer, the term of this patent is extended or adjusted under 35 U.S.C. 154(b) by 220 days.

This patent is subject to a terminal disclaimer.

(21) Appl. No.: 12/989,029

(22) PCT Filed: Apr. 20, 2009

(86) PCT No.: PCT/JP2009/057860
§ 371 (c)(1),
(2), (4) Date: Oct. 21, 2010

(87) PCT Pub. No.: WO2009/131098
PCT Pub. Date: Oct. 29, 2009

(65) Prior Publication Data
US 2011/0039813 A1  Feb. 17, 2011

(30) Foreign Application Priority Data
Apr. 22, 2008  (JP) ................. 2008-111295

(51) Int. Cl.
*A61K 45/06* (2006.01)
*A61K 31/194* (2006.01)
*A61K 31/42* (2006.01)
*A61K 31/423* (2006.01)
*A61K 31/519* (2006.01)
*A61K 31/5377* (2006.01)
*A61K 31/573* (2006.01)

(52) U.S. Cl.
CPC .............. *A61K 45/06* (2013.01); *A61K 31/194* (2013.01); *A61K 31/42* (2013.01); *A61K 31/423* (2013.01); *A61K 31/519* (2013.01); *A61K 31/5377* (2013.01); *A61K 31/573* (2013.01)

(58) Field of Classification Search
USPC ............ 514/179, 379, 239.2, 568, 378, 262.1
See application file for complete search history.

(56) References Cited

U.S. PATENT DOCUMENTS

| 6,608,101 | B1 | 8/2003 | Ni et al. |
| 7,772,285 | B2 | 8/2010 | Chaki et al. |
| 2004/0248865 | A1 | 12/2004 | Harris et al. |
| 2009/0099369 | A1 | 4/2009 | Yonezawa et al. |
| 2009/0163562 | A1 | 6/2009 | Kakuda et al. |
| 2009/0275757 | A1 | 11/2009 | Yonezawa et al. |
| 2010/0240891 | A1 | 9/2010 | Aikawa et al. |

FOREIGN PATENT DOCUMENTS

| JP | 2003 40776 | 2/2003 |
| JP | 2004 501147 | 1/2004 |
| JP | 2007 500223 | 1/2007 |
| RU | 2238933 C2 | 9/2003 |
| WO | 03 042150 | 5/2003 |
| WO | WO 2004/103365 A1 | 12/2004 |
| WO | WO 2007/138997 A1 | 12/2007 |

OTHER PUBLICATIONS

Cutolo (Anti-inflammatory mechanisms of methotrexate in rheumatoid arthritis, Amm Rheom Dis 2001; 60: pp. 729-735).*
Olson (Juvenile Idiopathic Arthritis: An Update, Wisconsin Medical Journal, 2006, pp. 45-51).*
Kavanaugh (Defining remission in psoriatic arthritis, Clinical and Experimental Rheumatology, 2006, S-83-87.*
U.S. Appl. No. 12/934,572, filed Sep. 24, 2010, Aikawa, et al.
Eric-Jan A. Kroot, et al., "Oral Pulsed Dexamethasone Therapy in Early Rheumatoid Arthritis: A Pilot Study", Annals New York Academy of Sciences, vol. 1069, XP 2656569, Jun. 2006, pp. 300-306.
Angelo Ravelli, et al., "Radiologic progression in patients with juvenile chronic arthritis treated with methotrexate", The Journal of Pediatrics, vol. 133, No. 2, XP 27398734, Aug. 1998, pp. 262-265.
Aikawa, Yukihiko et al., "Treatment of arthritis with a selective inhibitor of c-Fos/activator protein-1", Nature Biotechnology, vol. 26, No. 7, pp. 817-823, (Jul. 2008).
Katzung, G. Bertram: Immunopharmacology, Chapter 56, Basic & Clinical Pharmacology, Ninth Edition, McGraw-Hill Companies, pp. 940-950, (2004).
O'Dell, R. James et al., "Treatment of Rheumatoid Arthritis With Methotrexate Alone, Sulfasalazine and Hydroxychloroquine, or a Combination of All Three Medications", The New England Journal of Medicine, vol. 334, No. 20, pp. 1287-1291, (May 16, 1996).
U.S. Appl. No. 13/287,375, filed Nov. 2, 2011, Aikawa, et al.
Russian Office Action issued Dec. 14, 2012, in Russia Patent Application No. 2010147396/15 (068469) (with English translation).
V. M. Kevra, "Use of slowly effecting agents in complex therapy of patients affected by rheumatoid arthritis", Medicinal News, No. 9, 2005, pp. 83-86.

(Continued)

Primary Examiner — Kathrien Cruz
(74) Attorney, Agent, or Firm — Oblon, McClelland, Maier & Neustadt, L.L.P.

(57) ABSTRACT

Disclosed are use of a benzophenone derivative represented by general formula (I) or a salt thereof and one or more immunosuppressing agents in combination, and a pharmaceutical composition containing the benzophenone derivative or a salt thereof and one or more immunosuppressing agents. The use and the composition are useful for treatment or prevention of autoimmune diseases and the like. (In the formula, $R^1$ represents an optionally substituted heterocyclic group, a substituted phenyl group or the like; Z represents an alkylene group or the like; $R^2$ represents a carboxyl group, which may be protected by an alkyl group, or the like; $R^3$ represents an optionally protected hydroxyl group or the like; $R^4$ represents an optionally substituted cycloalkyloxy group or the like; and $R^5$ represents a hydrogen atom or the like.)

4 Claims, No Drawings

(56) References Cited

OTHER PUBLICATIONS

Sadao Kashiwazaki, "New strategies for treatment of rheumatoid arthritis", Nippon Rinsho, vol. 55, No. 9, 1997, pp. 283-291 (with English Abstract).

K. Faarvang, et al., "Hydroxychloroquine and sulphasalazine alone and in combination in rheumatoid arthritis: A randomised double blind trial", Annals of the Rheumatic Diseases, 1993, vol. 52, pp. 711-715.

D. Felson, et al., "The efficacy and toxicity of combination therapy in rheumatoid arthritis", Arthritis & Rheumatism, 1994, vol. 37, No. 10, pp. 1487-1491.

C. Haagsma, et al., "Combination of sulphasalazine and methotrexate versus the single components in early rheumatoid arthritis: A randomized controlled, double-blind, 52 week clinical trial*&", British Journal of Rheumatology, 1997, vol. 36, pp. 1082-1088.

Extended European Search Report issued Aug. 22, 2011, in Patent Application No. 09735250.4.

Eric-Jan A. Kroot, et al., "Oral Pulsed Dexamethasone Therapy in Early Rheumatoid Arthritis: A Pilot Study", Annals New York Academy of Sciences. vol. 1069, XP 2656569, Jun. 2006, pp. 300-306.

Angelo Revell. et al., "Radiologic progression in patients with juvenile chronic arthritis treated with methotrexate". The Journal of Pediatrics, vol. 133. No. 2, XP 27398734, Aug. 1998, pp. 262-265.

Office Action issued Dec. 26, 2011 in Chinese Application No. 200980114448.3 (With English Translation).

Wu Qiyan, et al., "Amelioration of knee joint function by intra-articular injection of methotrexate and dexamethasone in patients with rheumatoid", Chinese Journal of Clinical Rehabilitation, vol. 9, No. 27, Jul. 21, 2005, pp. 27-29 (With English Abstract).

* cited by examiner

METHOD OF UTILIZATION OF COMBINATION OF BENZOPHENONE DERIVATIVE OR SALT THEREOF AND IMMUNOSUPPRESSING AGENT, AND PHARMACEUTICAL COMPOSITION COMPRISING THESE COMPONENTS

TECHNICAL FIELD

The present invention relates to a method of using a benzophenone derivative or a salt thereof and an immunosuppressing agent in combination for the treatment such as the cure or prevention of autoimmune diseases. In addition, the present invention also relates to a pharmaceutical composition containing a benzophenone derivative or a salt thereof and an immunosuppressing agent useful for the treatment such as the cure or prevention of autoimmune diseases.

BACKGROUND ART

Autoimmune diseases, such as arthritis diseases in connective tissue disorders typified by rheumatoid arthritis cause, for example, dysfunction as a result of the progression of the destruction of cartilage and/or bone, and thus, this disease largely affects daily life.

To date, for the drug treatment of rheumatoid arthritis and other types of arthritis, nonsteroidal anti-inflammatory drugs (NSAIDs) such as aspirin and indomethacin, gold preparation, disease-modifying anti-rheumatoid drugs (DMARDs) such as D-penicillamine, steroidal drugs, and the like have been used. However, the progression of the destruction of cartilage and/or bone, which is the largest problem of arthritis, cannot be completely suppressed with the currently used treatment methods. Moreover, from the viewpoint of side effects, the aforementioned drugs cannot be used for a long period of time. Thus, these treatment methods have not yet provided a satisfactory treatment.

As a drug exhibiting effects on autoimmune diseases, immunosuppressing agents have been known (Non-Patent Document 1). The immunosuppressing agents suppress arthritis through inhibiting the production of antibodies, the production of cytokine, proliferation of lymphocyte, and the like. As such immunosuppressing agent, methotrexate and dexamethasone have been placed on the market, and even at present, the research and development of drugs are being performed.

On the other hand, benzophenone derivatives having an antiarthritic action have been known. It has been known that these benzophenone derivatives inhibit a transcription factor AP-1, and as a result, have an excellent anti arthritic action (Patent Document 1).

Moreover, a method of using several anti-arthritis agents in combination has been known (Non-Patent Document 2). However, the number of anti-arthritis agents for such combined use is limited, and thus, satisfactory therapeutic effects have not been achieved.

Furthermore, a method of using an immunosuppressing agent and a benzophenone derivative having an antiarthritic action in combination has not been known at all.

PRIOR ART DOCUMENTS

Patent Document

PATENT DOCUMENT 1: International Publication No. WO03/042150 pamphlet

Non-Patent Document

NON-PATENT DOCUMENT 1: Bertram G. Katzung, Basic & Clinical Pharmacology, Ninth Edition, McGraw-Hill Companies, pp. 940-950 (2004)
NON-PATENT DOCUMENT 2: The New England Journal of Medicine (N. Engl. J. Med.), vol. 334, pp. 1.287-1291 (1996)

OUTLINE OF THE INVENTION

Problems to be Solved by the Invention

It has been desired to develop a method useful for the treatment such as the cure or prevention of autoimmune diseases, and a pharmaceutical composition useful for the treatment such as the cure or prevention of autoimmune diseases.

Means for Solving the Problems

Under the aforementioned circumstances, as a result of intensive studies, the present inventors have discovered that a method of using a benzophenone derivative represented by the general formula [1] below or a salt thereof and one or more immunosuppressing agents in combination is useful as a method for the treatment such as the cure or prevention of autoimmune diseases:

[Formula 1]

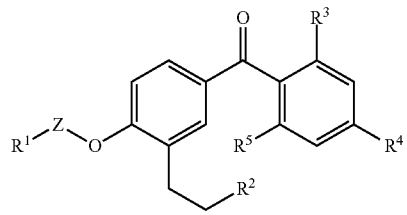

[1]

wherein $R^1$ represents a heterocyclic group which may be substituted, a substituted phenyl group or an alkyl group which may be substituted; Z represents an alkylene group which may be substituted; $R^2$ represents a heterocyclic group which may be substituted, an alkoxycarbonyl or heterocyclic carbonyl group which may be substituted, or a carboxyl group which may be protected; $R^3$ represents a hydrogen atom, a halogen atom, a cyano group, a nitro group, a carboxyl group which may be protected, a hydroxyl group which may be protected, an amino group which may be protected, a mercapto group, a carbamoyl group, or an alkyl, alkenyl, cycloalkyl, aryl, aralkyl, alkoxy, aryloxy, acyl, oxycarbonyl, aryloxycarbonyl, alkylthio, alkylsulfinyl, alkylsulfonyl, alkylamino, acylamino, alkylsulfonylamino, arylsulfonylamino or heterocyclic group which may be substituted; $R^4$ represents an alkoxy, cycloalkyloxy, cycloalkenyloxy, alkyl, cycloalkyl, heterocyclic-oxy or heterocyclic group which may be substituted; and $R^5$ represents a hydrogen atom, a halogen atom, or a hydroxyl group. Further, the inventors have discovered that a pharmaceutical composition containing these substances is useful for the treatment such as the cure or prevention of autoimmune diseases. Thus, the inventors have completed the present invention.

Advantages of the Invention

The method of using the benzophenone derivative represented by the general formula [1] or the salt thereof and one or more immunosuppressing agents in combination is useful as a method for the treatment such as the cure or prevention of autoimmune diseases, and the pharmaceutical composition containing these substances is useful for the treatment such as the cure or prevention of autoimmune diseases.

MODE FOR CARRYING OUT THE INVENTION

The present invention will be described in detail below.

In the present description, each term has the following meanings, unless otherwise specified.

A halogen atom refers to a fluorine atom, a chlorine atom, a bromine atom and an iodine atom; an alkyl group refers to, for example, a linear or branched $C_{1-12}$ alkyl group such as methyl, ethyl, n-propyl, isopropyl, n-butyl, sec-butyl, isobutyl, tert-butyl, pentyl, isopentyl, hexyl, heptyl and octyl; a lower alkyl group refers to, for example, a linear or branched $C_{1-6}$ alkyl group such as methyl, ethyl, n-propyl, isopropyl, n-butyl, sec-butyl, isobutyl, tert-butyl, pentyl and isopentyl; a halogeno lower alkyl group refers to, for example, a linear or branched halogeno-$C_{1-6}$ alkyl group such as fluoromethyl, chloromethyl, bromomethyl, dichloromethyl, trifluoromethyl, trichloromethyl, chloroethyl, dichloroethyl, trichloroethyl and chloropropyl; a lower alkoxy lower alkyl group refers to, for example, a linear or branched $C_{1-6}$ alkoxy-$C_{1-6}$ alkyl group such as methoxymethyl, ethoxymethyl, n-propoxymethyl, methoxyethyl and ethoxyethyl; a hydroxy lower alkyl group refers to, for example, a linear or branched hydroxy-$C_{1-6}$ alkyl group such as hydroxymethyl, hydroxyethyl and hydroxypropyl; and an amino lower alkyl group refers to, for example, an amino-$C_{1-6}$ alkyl group such as aminomethyl, aminoethyl and aminopropyl.

An alkenyl group refers to, for example, a linear or branched $C_{2-12}$ alkenyl group such as vinyl, allyl, propenyl, isopropenyl, butenyl, isobutenyl, pentenyl, hexenyl, heptenyl and octenyl; and a lower alkenyl group refers to, for example, a linear or branched $C_{2-6}$ alkenyl group such as vinyl, allyl, propenyl, isopropenyl, butenyl, isobutenyl and pentenyl.

A cycloalkyl group refers to, for example, a $C_{3-7}$ cycloalkyl group such as cyclopropyl, cyclobutyl, cyclopentyl, cyclohexyl and cycloheptyl; a cycloalkyloxy group refers to, for example, a $C_{3-7}$ cycloalkyloxy group such as cyclopropyloxy, cyclobutyloxy, cyclopentyloxy, cyclohexyloxy and cyclopentyloxy; and a cycloalkenyloxy group refers to, for example, a $C_{5-7}$ cycloalkenyloxy group such as cyclopentenyloxy and cyclohexenyloxy.

An aryl group refers to, for example, phenyl, tolyl and naphthyl; and an aralkyl group refers to, for example, an ar-$C_{1-12}$ alkyl group such as benzyl, diphenylmethyl, trityl, phenethyl, 4-methylbenzyl and naphthylmethyl.

An aryloxy group refers to, for example, phenoxy and naphthoxy; and an aryloxycarbonyl group refers to, for example, phenoxycarbonyl and naphthoxycarbonyl.

An alkoxy group refers to, for example, a linear or branched $C_{1-12}$ alkoxy group such as methoxy, ethoxy, n-propoxy, isopropoxy, n-butoxy, isobutoxy, sec-butoxy, tert-butoxy, pentyloxy, isopentyloxy, hexyloxy, heptyloxy and octyloxy; a lower alkoxy group refers to, for example, a linear or branched $C_{1-6}$ alkoxy group such as methoxy, ethoxy, n-propoxy, isopropoxy, n-butoxy, isobutoxy, sec-butoxy, tert-butoxy, pentyloxy and isopentyloxy; and an alkoxyalkyl group refers to, for example, methoxymethyl, ethoxymethyl and 2-(trimethylsilyl)ethoxymethyl.

An alkylene group refers to, for example, a linear or branched $C_{1-12}$ alkylene group such as methylene, ethylene and propylene.

An alkoxycarbonyl group refers to, for example, a linear or branched $C_{1-12}$ alkoxycarbonyl group such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl and pentyloxycarbonyl; a lower alkoxycarbonyl group refers to, for example, a linear or branched $C_{1-6}$ alkyloxycarbonyl group such as methoxycarbonyl, ethoxycarbonyl and propoxycarbonyl; a lower alkoxycarbonyl lower alkyl group refers to, for example, a linear or branched $C_{1-6}$ alkoxycarbonyl-$C_{1-6}$ alkyl group such as methoxycarbonylmethyl, ethoxycarbonylmethyl, n-propoxycarbonylmethyl, methoxycarbonylethyl and ethoxycarbonylethyl; and an aralkyloxycarbonyl group refers to, for example, an ar-$C_{1-12}$ alkyloxycarbonyl group such as benzyloxycarbonyl and 4-methylbenzyloxycarbonyl.

A lower alkoxyimino group refers to, for example, a linear or branched $C_{1-6}$ alkoxyimino group such as methoxyimino and ethoxyimino; an alkylamino group refers to, for example, a linear or branched $C_{1-12}$ alkylamino group such as methylamino, ethylamino, propylamino, butylamino, pentylamino, hexylamino, heptylamino and octylamino; a lower alkylamino group refers to, for example, a linear or branched mono- or di-$C_{1-6}$ alkylamino group such as methylamino, ethylamino, propylamino, dimethylamino, diethylamino and methylethylamino; a lower alkylamino lower alkyl group refers to, for example, a mono- or di-$C_{1-6}$ alkylamino-$C_{1-6}$ alkyl group such as methylaminomethyl, methylaminoethyl, ethylaminomethyl, methylaminopropyl, propylaminoethyl, dimethylaminomethyl, diethylaminomethyl, diethylaminoethyl and dimethylaminopropyl; and a lower alkylidene group refers to, for example, a $C_{1-6}$ alkylidene group such as methylene, ethylidene, propylidene and isopropylidene.

A nitrogen-containing heterocyclic group refers to, for example, a 5- or 6-membered ring, condensed ring, or crosslinked ring heterocyclic group, which contains one or more nitrogen atoms as heteroatoms for forming the ring and which may further contain one or more oxygen atoms or sulfur atoms, such as pyrrolyl, pyrrolidinyl, piperidyl, piperazinyl, imidazolyl, pyrazolyl, pyridyl, tetrahydropyridyl, pyrimidinyl, morpholinyl, thiomorpholinyl, quinolyl, quinolizinyl, tetrahydroquinolinyl, tetrahydroisoquinolinyl, quinuclidinyl, quinazolyl, thiazolyl, tetrazolyl, thiadiazolyl, pyrrolinyl, imidazolinyl, imidazolidinyl, pyrazolinyl, pyrazolidinyl, purinyl and indazolyl groups.

A heterocyclic group refers to, the aforementioned nitrogen-containing heterocyclic groups, and also, for example, a 5- or 6-membered ring, condensed ring, or crosslinked ring heterocyclic group, which contains at least one heteroatom selected from nitrogen, oxygen and sulfur atoms, and which may contain one or more oxygen atoms or sulfur atoms as heteroatoms for forming the ring, such as furyl, thienyl, 4-methyl-2-oxo-1,3-dioxole, benzothienyl, pyranyl, isobenzofuranyl, oxazolyl, benzofuranyl, indolyl, benzimidazolyl, benzoxazolyl, benzisoxazolyl, benzothiazolyl, quinoxalyl, dihydroquinoxalinyl, 2,3-dihydrobenzothienyl, 2,3-dihydrobenzopyrrolyl, 2,3-dihydro-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isoxazolyl, thiadiazolyl, oxadiazolyl, pyridazinyl, isoindolyl and isoquinolyl groups; and a heterocyclic carbonyl group refers to, for example, a heterocyclic —CO— group such as 4-hydroxy-2-(5H)-furanocarbonyl, morpholinocarbonyl, piperazinocarbonyl and pyrrolidinocarbonyl groups.

An acyl group refers to, for example, a formyl group, a linear or branched $C_{2-12}$ alkanoyl group such as acetyl, isovaleryl, propionyl and pivaloyl, an aralkylcarbonyl group such as benzylcarbonyl, an aroyl group such as benzoyl and naphthoyl, and a heterocyclic carbonyl group such as nicotinoyl, thenoyl, pyrrolidinocarbonyl and furoyl groups; and an acylamino group refers to, for example, a $C_{1-6}$ acylamino group such as formylamino, acetylamino, propionylamino and butyrylamino.

A cyclic amino group may refer to, for example, any of saturated cyclic amino and unsaturated cyclic amino groups, and it may further contain one or more heteroatoms such as nitrogen atoms, oxygen atoms and sulfur atoms and carbonyl carbons in the ring thereof, and it may also be a monocyclic, bicyclic or tricyclic group. More specifically, such cyclic amino group refers to: a saturated or unsaturated monocyclic 3- to 7-membered cyclic amino group having one nitrogen atom, such as aziridin-1-yl, azetidin-1-yl, pyrrolidin-1-yl, pyrrolin-1-yl, pyrrol-1-yl, dihydropyridin-1-yl, piperidin-1-yl, dihydroazepin-1-yl and perhydroazepin-1-yl; a saturated or unsaturated monocyclic 3- to 7-membered cyclic amino group having two nitrogen atoms, such as imidazol-1-yl, imidazolidin-1-yl, imidazolin-1-yl, pyrazolidin-1-yl, piperazin-1-yl, 1,4-dihydropyrazin-1-yl, 1,2-dihydropyrimidin-1-yl, perhydropyrazin-1-yl and homopiperazin-1-yl, a saturated or unsaturated monocyclic 3- to 7-membered cyclic amino group having three or more nitrogen atoms, such as 1,2,4-triazol-1-yl, 1,2,3-triazol-1-yl, 1,2-dihydro-1,2,4-triazin-1-yl and perhydro-S-triazin-1-yl; a saturated or unsaturated monocyclic 3- to 7-membered cyclic amino group having 1 to 4 heteroatoms selected from oxygen atoms and sulfur atoms, in addition to nitrogen atoms, such as oxazolidin-3-yl, isoxazolidin-2-yl, morpholin-4-yl, thiazolidin-3-yl, isothiazolidin-2-yl, thiomorpholin-4-yl, homothiomorpholin-4-yl and 1,2,4-thiadiazolin-2-yl; a saturated or unsaturated, bicyclic or tricyclic amino group, such as isoindolin-2-yl, indolin-1-yl, 1H-indazol-1-yl, purin-7-yl and tetrahydroquinolin-1-yl; and a spiro or crosslinked, saturated or unsaturated 5- to 12-membered cyclic amino group, such as 5-azaspiro[2.4]heptan-5-yl, 2,8-diazabicyclo[4.3.0]nonan-8-yl, 3-azabicyclo[3.1.0]hexan-3-yl, 2-oxa-5,8-diazabicyclo[4.3.0]nonan-8-yl, 2,8-diazaspiro[4.4]nonan-2-yl and 7-azabicyclo[2.2.1]heptan-7-yl.

An alkylthio group refers to, for example, a linear or branched $C_{1-12}$ alkylthio group such as methylthio, ethylthio, n-propylthio, isopropylthio, n-butylthio, isobutylthio, sec-butylthio, tert-butylthio, pentylthio, isopentylthio, hexylthio, heptylthio and octylthio; and a lower alkylthio group refers to, for example, a linear or branched $C_{1-6}$ alkylthio group such as methylthio, ethylthio, n-propylthio, isopropylthio, n-butylthio, isobutylthio, sec-butylthio, tert-butylthio, pentylthio and isopentylthio.

An alkylsulfinyl group refers to, for example, a linear or branched $C_{1-12}$ alkylsulfinyl group such as methylsulfinyl, ethylsulfinyl, n-propylsulfinyl, isopropylsulfinyl, n-butylsulfinyl, isobutylsulfinyl, sec-butylsulfinyl, tert-butylsulfinyl, pentylsulfinyl, isopentylsulfinyl, hexylsulfinyl, heptylsulfinyl and octylsulfinyl; an alkylsulfonyl group refers to, for example, a linear or branched $C_{1-12}$ alkylsulfonyl group such as methylsulfonyl, ethylsulfonyl, n-propylsulfonyl, isopropylsulfonyl, n-butylsulfonyl, isobutylsulfonyl, sec-butylsulfonyl, tert-butylsulfonyl, pentylsulfonyl, isopentylsulfonyl, hexylsulfonyl, heptylsulfonyl and octylsulfonyl; and an arylsulfonyl group refers to, for example, benzenesulfonyl and p-toluenesulfonyl.

An alkylsulfonylamino group refers to, for example, a linear or branched $C_{1-12}$ alkylsulfonylamino group such as methylsulfonylamino, ethylsulfonylamino, n-propylsulfonylamino, isopropylsulfonylamino, n-butylsulfonylamino, isobutylsulfonylamino, sec-butylsulfonylamino, tert-butylsulfonylamino, pentylsulfonylamino, isopentylsulfonylamino, hexylsulfonylamino, heptylsulfonylamino and octylsulfonylamino; and an arylsulfonylamino group refers to, for example, an aryl-SO$_2$NH— group such as phenylsulfonylamino and naphthylsulfonylamino.

A lower alkylsulfinyl group refers to, for example, a linear or branched $C_{1-6}$ alkylsulfinyl group such as methylsulfinyl, ethylsulfinyl, n-propylsulfinyl, isopropylsulfinyl, n-butylsulfinyl, isobutylsulfinyl, sec-butylsulfinyl, tert-butylsulfinyl, pentylsulfinyl and hexylsulfinyl; and a lower alkylsulfonyl group refers to, for example, a linear or branched $C_{1-6}$ alkylsulfonyl group such as methylsulfonyl, ethylsulfonyl, n-propylsulfonyl, isopropylsulfonyl, n-butylsulfonyl, isobutylsulfonyl, sec-butylsulfonyl, tert-butylsulfonyl and pentylsulfonyl.

A lower alkylcarbamoyl group refers to, for example, a mono- or di-$C_{1-6}$ alkylcarbamoyl group such as methylcarbamoyl, ethylcarbamoyl, propylcarbamoyl, dimethylcarbamoyl, diethylcarbamoyl and methylethylcarbamoyl; and a lower alkylsulfonylamino group refers to, for example, a linear or branched $C_{1-6}$ alkylsulfonylamino group such as methylsulfonylamino, ethylsulfonylamino, n-propylsulfonylamino, isopropylsulfonylamino, n-butylsulfonylamino, isobutylsulfonylamino, sec-butylsulfonylamino, tert-butylsulfonylamino and pentylsulfonylamino.

A lower alkylsulfonylcarbamoyl group refers to, for example, a linear or branched $C_{1-6}$ alkylsulfonylcarbamoyl group such as methylsulfonylcarbamoyl, ethylsulfonylcarbamoyl, n-propylsulfonylcarbamoyl, isopropylsulfonylcarbamoyl, n-butylsulfonylcarbamoyl, isobutylsulfonylcarbamoyl, sec-butylsulfonylcarbamoyl, tert-butylsulfonylcarbamoyl and pentylsulfonylcarbamoyl; and a lower alkylaminosulfonyl group refers to, for example, a mono- or di-$C_{1-6}$ alkylaminosulfonyl group such as methylaminosulfonyl, ethylaminosulfonyl, propylaminosulfonyl, dimethylaminosulfonyl, diethylaminosulfonyl and methylethylaminosulfonyl.

A carboxyl lower alkenyl group refers to, for example, a linear or branched $C_{2-6}$ alkenyl group substituted with a carboxyl group.

A lower alkyl heterocyclic group refers to, for example, a heterocyclic group substituted with a linear or branched lower alkyl group; and a hydroxy heterocyclic group refers to, for example, a heterocyclic group substituted with a hydroxyl group.

A lower alkoxy lower alkoxy group refers to a linear or branched $C_{1-6}$ alkoxy group substituted with a lower alkoxy group.

A heterocyclic-oxy group refers to groups represented by heterocyclic —O—, bound via oxygen atoms, such as pyrrolidinyloxy, piperidinyloxy, tetrahydrofuranyloxy, tetrahydropyranyloxy and tetrahydrothiopyranyloxy.

A carboxyl protective group includes any group which can be normally used as a protective group of a carboxyl group, for example, the groups described in W. Greene et al. "Protective Groups in Organic Synthesis" Third Edition, pp. 369 to 453, 1999, John Wiley & Sons, INC. More specifically, examples of a carboxyl protective group include an alkyl group, an alkenyl group, an aryl group, an aralkyl group, a cycloalkyl group and an alkoxyalkyl group.

An amino protective group includes any group which can be normally used as a protective group of an amino group, for example, the groups described in W. Greene et al. "Protective Groups in Organic Synthesis" Third Edition, pp. 494 to 615, 1999, John Wiley & Sons, INC. More specifically, examples of an amino protective group include an acyl group, an alkoxycarbonyl group, an aralkyloxycarbonyl group, an aryloxy carbonyl group, an aralkyl group, an alkoxyalkyl group, an alkylsulfonyl group and an arylsulfonyl group.

A hydroxyl protective group includes any group which can be normally used as a protective group of a hydroxyl group, for example, the groups described in W. Greene et al. "Protective Groups in Organic Synthesis" Third Edition, pp. 17 to 245, 1999, John Wiley & Sons, INC. More specifically, examples of a hydroxyl protective group include an acyl group, an alkoxycarbonyl group, an aralkyloxycarbonyl group, an alkyl group, an alkenyl group, an aralkyl group and an alkoxyalkyl group.

Each of the heterocyclic, phenyl and alkyl groups represented by $R^1$; the heterocyclic, alkoxycarbonyl and heterocyclic carbonyl groups represented by $R^2$; the alkyl, alkenyl, cycloalkyl, aryl, aralkyl, alkoxy, aryloxy, acyl, alkoxycarbonyl, aryloxycarbonyl, alkylthio, alkylsulfinyl, alkylsulfonyl, alkylamino, acylamino, alkylsulfonylamino, arylsulfonylamino and heterocyclic groups represented by $R^3$; and the alkoxy, cycloalkyloxy, cycloalkenyloxy, alkyl, cycloalkyl, heterocyclic-oxy and heterocyclic groups represented by $R^4$ may be further substituted with one or more groups selected from a cyano group, a nitro group, a halogen atom, carboxyl, phosphoryl, hydroxyl, amino, carbamoyl, hydroxycarbamoyl, aminosulfonyl, sulfo, hydroxy lower alkyl, amino lower alkyl, cyclic amino, lower alkylamino and lower alkylamino lower alkyl groups which may be protected, a lower alkyl group, a lower alkenyl group, a lower alkoxy group, a lower alkoxycarbonyl group, an acyl group, an aryl group, a heterocyclic group, a cycloalkyl group, an aralkyl group, a lower alkylidene group, a mercapto group, a lower alkylthio group, a lower alkylsulfinyl group, a lower alkylsulfonyl group, a lower alkylsulfonylcarbamoyl group, a lower alkylcarbamoyl group, a lower alkylsulfonylamino group, a lower alkylaminosulfonyl group, a carboxyl lower alkenyl group, a hydroxy heterocyclic group, a lower alkyl heterocyclic group, a lower alkoxy lower alkoxy group, a halogeno lower alkyl group, a lower alkoxy lower alkyl group, a lower alkoxycarbonyl lower alkyl group, and a lower alkoxyimino group.

The alkylene group represented by Z may be further substituted with one or more groups selected from a cyano group, a nitro group, a halogen atom, carboxyl, carbamoyl, hydroxycarbamoyl, hydroxy lower alkyl, amino lower alkyl and lower alkylamino lower alkyl groups which may be protected, a lower alkyl group, a lower alkoxycarbonyl group, an acyl group, an aryl group, a heterocyclic group, a cycloalkyl group, a lower alkenyl group, an aralkyl group, a lower alkylsulfonylcarbamoyl group, a lower alkylcarbamoyl group, a halogen lower alkyl group, a lower alkoxy lower alkyl group and a lower alkoxycarbonyl lower alkyl group.

The aforementioned each substituent may be further substituted with the groups exemplified as substituents for each substituent.

In addition, the heterocyclic group and cyclic amino group for each substituent may be further substituted with a keto group.

The salt of the compound of the general formula [1] includes commonly known salts formed with a basic group such as an amino group, or with an acidic group such as a hydroxyl or carboxyl group.

Examples of salts formed with a basic group include salts with mineral acid such as hydrochloric acid, hydrobromic acid, nitric acid and sulfuric acid; salts with organic carboxylic acid such as formic acid, acetic acid, citric acid, oxalic acid, fumaric acid, maleic acid, succinic acid, malic acid, tartaric acid, aspartic acid, trichloroacetic acid and trifluoroacetic acid; and salts with sulfonic acid such as methanesulfonic acid, benzenesulfonic acid, p-toluenesulfonic acid, mesitylenesulfonic acid and naphthalenesulfonic acid.

Examples of salts formed with an acidic group include salts with alkaline metal such as sodium and potassium; salts with alkaline earth metal such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine and N,N'-dibenzylethylenediamine.

Moreover, among the above described salts, a preferable salt of the compound of the general formula [1] is a pharmaceutically acceptable salt thereof.

When isomers (for example, optical isomers, geometric isomers, and tautomers) exist in the benzophenone derivative represented by the general formula [1] or the salt thereof, the present invention includes all such isomers, and also includes hydrates, solvates and all crystals.

Preferred compounds as the benzophenone derivative represented by the general formula [1] or the salt thereof are as follows.

The compound wherein $R^1$ is a heterocyclic group which may be substituted or a substituted phenyl group is preferable. The compound wherein $R^1$ is a heterocyclic group which may be substituted is more preferable.

The compound wherein $R^2$ is a carboxyl group which may be protected with an alkyl group is preferable. The compound wherein $R^2$ is a carboxyl group is more preferable.

The compound wherein $R^3$ is a hydroxyl group which may be protected is preferable. The compound wherein $R^3$ is a hydroxyl group is more preferable.

The compound wherein $R^4$ is a cycloalkyloxy group which may be substituted is preferable. The compound wherein $R^4$ is a cycloalkyloxy group is more preferable.

The compound wherein $R^5$ is a hydrogen atom is preferable.

The compound wherein Z is an alkylene group is preferable, and the compound wherein Z is a methylene group is more preferable.

Preferred benzophenone derivatives represented by the general formula [1] include: 2-(4-morpholinyl)ethyl 3-(5-(4-(cyclopentyloxy)-2-hydroxybenzoyl)-2-((3-hydroxy-1,2-benzisoxazol-6-yl)methoxy)phenyl)propionate; 4-(2-(2-carboxyethyl)-4-(4-(cyclopentyloxy)-2-hydroxybenzoyl)phenoxy)methyl)benzoic acid; 3-(5-(4-(cyclopentyloxy)-2-hydroxybenzoyl)-2-((4-(3-hydroxy-5-isoxazolyl)benzyl)oxy)phenyl)propionic acid; and 3-(5-(4-(cyclopentyloxy)-2-hydroxybenzoyl)-2-(3-hydroxy-1,2-benzisoxazol-6-yl)methoxy)phenyl)propionic acid; or the salts thereof. Of these, 3-(5-(4-(cyclopentyloxy)-2-hydroxybenzoyl)-2-((3-hydroxy-1,2-benzisoxazol-6-yl)methoxy)phenyl)propionic acid or the salt thereof are more preferable.

The benzophenone derivative represented by the general formula [1] is produced by combining known methods. For example, it can be produced by the method described in Patent Document 1.

The autoimmune diseases in the present invention include: arthritis diseases such as rheumatoid arthritis, juvenile idiopathic arthritis and psoriatic arthritis; inflammatory bowel diseases such as ulcerative colitis and Crohn's disease; systemic lupus erythematosus; scleroderma; Behcet's disease; rheumatic fever; polymyositis; periarteritis nodosa; Sjogren's syndrome; active chronic hepatitis; and glomerular nephritis. Of these diseases, the arthritis diseases are preferable, and rheumatoid arthritis is more preferable.

Examples of the immunosuppressing agent used in the present invention include metabolic antagonists, such as methotrexate, azathioprine and mizoribine, and compounds showing an immunosuppression, such as steroidal anti-inflammatory drugs such as dexamethasone, prednisolone and cortisone acetate. Methotrexate and dexamethasone are more preferable.

The administration route of the pharmaceutical composition of the present invention is not particularly limited. The present pharmaceutical composition can be administered via intravenous, oral, intramuscular, subcutaneous, inhalation, spraying, or other administration routes. Moreover, the benzophenone derivative represented by the general formula [1] or the salt thereof may be administered at the same time with the immunosuppressing agent, or in a specific order.

The method of using the benzophenone derivative represented by the general formula [1] or the salt thereof and one or more immunosuppressing agents in combination according to the present invention is useful as a method for the treatment such as the cure or prevention of autoimmune diseases. In addition, this method is more usefully used for the cure of the aforementioned disease.

Moreover, a pharmaceutical composition containing the benzophenone derivative represented by the general formula [1] or the salt thereof and one or more immunosuppressing agents is useful for the treatment such as the cure or prevention of autoimmune diseases. Furthermore, this pharmaceutical composition is more usefully used for the cure of the aforementioned disease.

According to the method and pharmaceutical composition of the present invention, the treatment such as the cure or prevention of more severe autoimmune diseases become possible. Further, even if the amounts of individual agents used are reduced and then administered, the pharmaceutical composition still exhibits a strong action. Thus, it becomes possible to reduce the side effects of individual agents.

When the pharmaceutical composition of the present invention is used, formulation additives such as excipients, carriers and dilution agents, which are generally used for formulation, may be appropriately mixed with the present pharmaceutical composition. According to an ordinary method, these compositions may be formulated as tablets, capsules, powders, syrups, granules, pills, suspensions, emulsions, liquids, powder formulations, suppositories, eye drops, nose drops, ear drops, adhesive skin patches, ointments, injections and the like, and may be administered either orally or parenterally. In addition, after each active ingredient was separately formulated as a kit, each of these may be separately administered in the same route or different routes at the same time or temporal difference. Moreover, the administration method, dosage and the number of doses of the preparations may be arbitrarily determined in accordance with the age and weight of the patient, and the severity of the patient's symptoms. The recommended dose range for adult patients is generally 0.01 to 1000 mg/kg/day via oral administration or parenteral administration (for example, injection, intravenous drip and rectal administration) either once or divided over several administrations, or by administering the doses for several days at one time.

EXAMPLES

The present invention will be described in the following test examples. However, these examples are not intended to limit the scope of the present invention.

3-(5-(4-(cyclopentyloxy)-2-hydroxybenzoyl)-2-((3-hydroxy-1,2-benzisoxazol-6-yl)methoxy)phenyl)propionic acid (hereinafter referred to as compound A) was selected as a tested substance. Methotrexate and dexamethasone were selected as immunosuppressing agents.

Test Example 1

Effects of the Combined Use of Compound A and Methotrexate on Mouse Type II Collagen-Induced Arthritis Compound A was selected as a tested substance. Methotrexate was selected as an immunosuppressing agent.

Eight-week-old male DBA/1J mice (9 or 10 mice per group; Charles River Laboratories Japan) were used. A 2 mg/mL bovine type II collagen dissolved in a 0.1 mol/L acetic acid solution (Koken Co., Ltd.) was mixed with an equal volume of Freund's complete adjuvant (BD Diagnostic Systems) to prepare an emulsion. The emulsion (0.2 mL) was intradermally injected at the hip of each mouse. Twenty-one days after the primary immunization, the same treatment was carried out (secondary immunization), so that type II collagen arthritis was induced.

Compound A was dissolved in a 2-fold molar amount of sodium hydroxide solution, and a 3-fold weight of polyvinylpyrrolidone was then added to the solution, followed by dilution with distilled water. The concentration of compound A in a compound A (1 mg/kg)-dosing solution was adjusted to be 0.1 mg/mL. Methotrexate was suspended in 0.5% methylcellulose solution. The concentration of methotrexate in methotrexate (0.5 mg/kg)-dosing solution was adjusted to be 0.05 mg/mL. Each dosing solution was orally administered to the mice.

To control group, polyvinylpyrrolidone solution and 0.5% methylcellulose solution were orally administered.

After dividing into groups, and the second immunization, compound A and methotrexate were administered once a day for 14 days.

The knuckle portion and the articulations of wrist and tarsus portions of the four paws of each mouse were evaluated using the following 4 scores. In a total of the four paws, the maximum arthritis score was set at 12 points.

0: no changes
1: swelling of one or two toes or a slight swelling of ankle
2: swelling of three or more toes, or moderate swelling of ankle
3: extensive swelling of paws In addition, the arthritis inhibition rate was obtained by the following formula:

Arthritis inhibition rate (%)=100−(the score of the tested substance−dosing group/the score of the control group)×100

The results of the arthritis on the day following the final administration are shown in Table 1.

TABLE 1

| Dosing group | Arthritis inhibition rate (%) |
|---|---|
| Compound A (1 mg/kg) | 19 |
| Methotrexate (0.5 mg/kg) | 15 |
| Compound A(1 mg/kg) and methotrexate (0.5 mg/kg) | 43 |

The arthritis inhibition rates of compound A (1 mg/kg)-dosing group was 19%, and the arthritis inhibition rates of methotrexate (0.5 mg/kg)-dosing group was 15%. In contrast, the arthritis inhibition rate of the group to which both compound A (1 mg/kg) and methotrexate (0.5 mg/kg) were applied in combination, was 43%. Thus, the combined use of compound A and methotrexate strongly inhibited arthritis.

Test Example 2

Effects of the Combined Use of Compound A and Dexamethasone on Mouse Type II Collagen-Induced Arthritis Compound A was selected as a tested substance. Dexamethasone was selected as an immunosuppressing agent.

Eight-week-old male DBA/1J mice (8-10 mice per group; Charles River Laboratories Japan) were used. The induction of mouse type II collagen arthritis was conducted by the method according to Test Example 1.

Compound A was dissolved in a 2-fold molar amount of sodium hydroxide solution, and a 3-fold weight of polyvinylpyrrolidone was then added to the solution, followed by dilution with distilled water. The concentrations of compound A in compound A (1 mg/kg and 10 mg/kg)-dosing solutions were adjusted to be 0.1 mg/mL and 1.0 mg/mL. The concentration of compound A in a compound A (1 mg/kg)-dosing solution in combined administration was adjusted to be 0.2 mg/mL. Dexamethasone was suspended in polyvinylpyrrolidone solution. The concentration of dexamethasone in dexamethasone (0.025 mg/kg)-dosing solution was adjusted to be 0.0025 mg/mL. The concentration of dexamethasone in dexamethasone (0.025 mg/kg)-dosing solution in combined administration was adjusted to be 0.005 mg/mL. Each dosing solution was orally administered to the mice.

To control group, polyvinylpyrrolidone solution was orally administered.

After dividing into groups, and the second immunization, compound A and dexamethasone were administered once a day for 14 days.

The evaluation to mouse arthritis was conducted by the method according to Test Example 1.

The results of the arthritis on the day following the final administration are shown in Table 2.

TABLE 2

| Dosing group | Arthritis inhibition rate (%) |
| --- | --- |
| Compound A (1 mg/kg) | 14 |
| Compound A (10 mg/kg) | 58 |
| Dexamethasone (0.025 mg/kg) | 30 |
| Compound A(1 mg/kg) and dexamethasone (0.025 mg/kg) | 66 |

The arthritis inhibition rates of compound A (1 mg/kg)-dosing group was 14%, and the arthritis inhibition rates of dexamethasone (0.025 mg/kg)-dosing group was 30%. In contrast, the arthritis inhibition rate of the group to which both compound A (1 mg/kg) and dexamethasone (0.025 mg/kg) were applied in combination, was 66%. Thus, the combined use of compound A and dexamethasone strongly inhibited arthritis.

The doses of compound A and dexamethasone in the combined use were low, namely, 1/10 of the high dose of compound A (10 mg/kg). However, the combined use of compound A and dexamethasone exhibited a strong anti-arthritic effect.

As is clear from the above results, a combined administration of the benzophenone derivative represented by the general formula [1] or the salt thereof and one or more immunosuppressing agents exhibits synergistic anti-arthritis effects, and thus it is useful for the treatment such as the cure or prevention of arthritis.

INDUSTRIAL APPLICABILITY

A method of using a benzophenone derivative or a salt thereof and one or more immunosuppressing agents in combination is useful as a method for the treatment such as the cure or prevention of autoimmune diseases. A pharmaceutical composition containing these substances is useful for the treatment such as the cure or prevention of autoimmune diseases.

The invention claimed is:

1. A method of treating rheumatoid arthritis, juvenile idiopathic arthritis or psoriatic arthritis, comprising administering to a subject in need thereof 1 mg/kg of 3-(5-(4-(cyclopentyloxy)-2-hydroxybenzoyl)-2-((3-hydroxy-1,2-benzisoxazol-6-yl)methoxy)phenyl)propionic acid or a salt thereof and 0.5 mg/kg of methotrexate in combination.

2. The method according to claim 1, wherein the subject has rheumatoid arthritis.

3. The method according to claim 1, wherein the subject has juvenile idiopathic arthritis.

4. The method according to claim 1, wherein the subject has psoriatic arthritis.

* * * * *